US007138089B2

(12) United States Patent
Aitken et al.

(10) Patent No.: US 7,138,089 B2
(45) Date of Patent: *Nov. 21, 2006

(54) TEST DEVICE FOR ANALYZING BLOOD GLUCOSE OR OTHER ANALYTES IN BODILY FLUIDS

(75) Inventors: James Aitken, Dartford (GB); Andrew James Woodhead, London (GB); Stuart Richard May, London (GB); Murdo M. Black, Ipswich (GB)

(73) Assignee: Hypoguard Limited, Suffolk (GB)

( * ) Notice: Subject to any disclaimer, the term of this patent is extended or adjusted under 35 U.S.C. 154(b) by 474 days.

This patent is subject to a terminal disclaimer.

(21) Appl. No.: 09/909,427

(22) Filed: Jul. 19, 2001

(65) Prior Publication Data

US 2002/0076349 A1   Jun. 20, 2002

(30) Foreign Application Priority Data

Jul. 20, 2000  (GB)  ................................. 0017737.8

(51) Int. Cl.
  *G01N 27/00*  (2006.01)
(52) U.S. Cl. .................. 422/82.01; 422/50; 422/56; 422/58; 422/63; 422/64; 422/66; 436/95
(58) Field of Classification Search ................ 422/58, 422/61, 63, 64, 66, 100, 102, 104; 436/44–46, 436/808
  See application file for complete search history.

(56) References Cited

U.S. PATENT DOCUMENTS

| 4,279,861 A | * | 7/1981 | Jessop ........................ 422/67 |
| 5,282,950 A | | 2/1994 | Dietze et al. |
| 5,395,504 A | | 3/1995 | Saurer et al. |
| 5,407,554 A | | 4/1995 | Saurer |
| 5,460,778 A | * | 10/1995 | Macindoe, Jr. .............. 422/63 |
| 5,525,297 A | | 6/1996 | Dinger et al. |
| 5,653,942 A | * | 8/1997 | Terashima et al. ............ 422/63 |
| 5,660,791 A | * | 8/1997 | Brenneman et al. .......... 422/58 |
| 5,797,693 A | | 8/1998 | Jaeger |
| 5,810,199 A | | 9/1998 | Charlton et al. |
| 5,872,713 A | | 2/1999 | Douglas et al. |
| 6,534,017 B1 | * | 3/2003 | Bottwein et al. ........... 422/104 |

FOREIGN PATENT DOCUMENTS

| DE | 2652370 | 5/1978 |
| DE | 29620368 U1 | 3/1997 |
| DE | 19639226 A1 | 3/1998 |
| DE | 19715031 A1 | 10/1998 |
| EP | 0373413 | 6/1990 |
| EP | 0455508 A1 | 11/1991 |
| EP | 0732590 A2 | 9/1996 |

(Continued)

*Primary Examiner*—Yelena G. Gakh
(74) *Attorney, Agent, or Firm*—Thompson Coburn LLP (57) ABSTRACT

A test device for testing of analyte concentration in a fluid to be applied thereto, the device comprising a plurality of test members arranged in at least one stack and electrodes for engaging with electrode tracks on a test member. A pusher pushes a single test member from the stack so that it can engage with the electrodes. An actuation member is connected to the pusher, and moves it when operated by a user. The at least one stack of test members is enclosed in a magazine which is initially sealed by a moisture impermeable seal. A cutter is provided for slitting the seal and permitting a test member to be pushed from the magazine by the pusher when the first test member from the magazine is to be used.

16 Claims, 11 Drawing Sheets

FOREIGN PATENT DOCUMENTS

| | | |
|---|---|---|
| EP | 0738666 A2 | 10/1996 |
| EP | 0811843 A2 | 12/1997 |
| EP | 0877250 A2 | 11/1998 |
| EP | 0909952 A2 | 4/1999 |
| WO | WO92/17778 | 10/1992 |
| WO | WO94/10558 | 5/1994 |
| WO | WO94/19685 | 9/1994 |
| WO | WO97/48979 | 12/1997 |
| WO | WO98/19159 | 5/1998 |
| WO | WO99/13100 | 3/1999 |

* cited by examiner

TEST DEVICE FOR ANALYZING BLOOD GLUCOSE OR OTHER ANALYTES IN BODILY FLUIDS

BACKGROUND OF THE INVENTION

1. Field of the Invention

The present invention relates to a test device for measuring the concentration of an analyte in a fluid sample, notably to a test device for analysing blood glucose or other analytes in bodily fluids.

2. Description of the Prior Art

Diabetics regularly need to test samples of their blood to determine the level of blood glucose. The results of such tests may be used to determine levels of medication needed to treat the diabetes at the time. In one known type of system, disposable sensors are used to test the blood. The sensors typically take the form of test strips which are provided with a reagent material that will react with blood glucose to produce an electrical signal. Conductive tracks on the test strip relay the electrical signal to a meter which displays the result. After a sample of blood has been applied to the test strip and the measurement has been taken, the test strip is disposed of. In order to couple the conductive tracks on a test strip with the meter, the test strip needs to be inserted into a sensor holder prior to the start of testing. The sensor holder has corresponding electrodes which are brought into electrical contact with the conductive tracks of the test strip. Test devices are known in which a plurality of test strip are provided on a cartridge disc. Each strip is housed in its own sensor slot, and means are provided to eject a test strip from its slot when required, and to automatically locate it in a sensor holder. Examples of test devices with test strip dispensers are described in U.S. Pat. No. 5,660,791, European Patent Application No. 0 732 590, and European Patent Application No. 0 738 666.

A problem with test strips is that they have only a limited shelf life, and exposure of test strips to the atmosphere reduces the shelf life further. Test strips open to the atmosphere will typically have a shelf life of about two to three months, whereas test strips which are sealed from the atmosphere will have a shelf life of about six to 12 months.

It has been proposed in WO 94/10558 to provide a stack of disposable test elements in a cylindrical housing, the stack being urged towards a test station to form a liquid-proof seal. In DE 196 39 226 A1 it is proposed to provide a test device with a cartridge that may have a plurality of chambers containing test strips, each of which chambers may be individually sealed to preserve the shelf life of the strips therein. A user removes the seal for each chamber when required, and a timing circuit may be activated either by the user or when the cartridge is pushed into the device. After a set time period has elapsed, an alarm or other indication reminds the user that the time period for using the strips has elapsed.

It is an object of the present invention to provide an improved test device.

SUMMARY OF THE INVENTION

According to one aspect of the present invention there is provided a test device for testing of analyte concentration in a fluid to be applied thereto, the device comprising:

a) a plurality of test members arranged in at least one stack, each of said test members carrying reagent means for producing an electrical signal in response to the concentration of analyte in an applied fluid, each of said test members having a plurality of electrode tracks for transmitting said electrical signal;

b) a housing having electrodes disposed therein for engaging with the electrode tracks on a test member at an engagement location;

c) a meter connected to the said electrodes and disposed at least partly in the housing, having electronics means for producing a signal output which is dependent on the electrical signal from a test member when the test member is engaged with the said electrodes;

d) a pusher which is adapted to push a single test member from the stack and into the engagement location where it can engage with the said electrodes and where the test member can be accessed to apply a fluid thereto;

e) an actuation member operably connected to the pusher, the said actuation member being operable by a user to move the pusher;

f) the or each stack of test members being enclosed in a magazine which is initially sealed by a moisture impermeable seal; and g) wherein means are provided for breaking the said seal and permitting a test member to be pushed from the magazine by the pusher when the first test member from the said magazine is to be used.

The device may be disposable and may be pre-loaded with all the test members. At the point of final assembly, test member and meter calibration constants, expiry date information and units of measurement may be downloaded into the meter by suitable means, for example via a bi-directional RS232 bus. This has the advantage that each meter may be uniquely matched to the specific batch of test members used within the device. The meter and associated test members can be quality controlled as a single unit and by removing the need for a user to input calibration data, as in a conventional meter, user error of this function may be eliminated.

The software may also prevent the device from being used outside the overall product expiry date and may be programmed to prevent test members from an opened magazine from being used beyond its specific expiry period.

Because the seal on a magazine is automatically broken only when the first test member is to be used, the shelf life of each stack is maximised, and the user is not required to take any action other than to operate the device.

The test members will typically be elongate test strips, and the invention will be described herein with reference to such test strips. However it will be understood that the test members may be of any desired shape and profile.

In a preferred embodiment, a plurality of magazines are provided in a movable cartridge. Each magazine is sealed until a test strip therein is required for use, whereupon the cartridge moves to bring the magazine into a position for use, and the seal is broken. This process is preferably automated and requires no user input. Any number of magazines may be employed, each containing any desired number of test strips. For example, each magazine may have 20 test strips and there may be 5 magazines, so that the device is usable for 100 readings before being discarded.

The actuation member may be mechanically linked to the pusher, directly or indirectly, or it may be linked electronically, for example by actuating an electric motor which drives the pusher. In a preferred embodiment the actuation member comprises a plunger which the user presses. The plunger may act on the pusher via another member, notably a sliding member which has a cam surface. It will be appreciated that many other suitable arrangements may also be employed.

The seal may be broken on one side by a blade past which the magazine is moved, to permit a test strip to be pushed out. The seal may be broken at the other side and along the top by one or more cutting surfaces at the leading edge of the pusher, so that the pusher initially both cuts the seal and pushes the top test strip to the engagement location. However, it would also be possible for the pusher to cause the test strip to break through the seal without the need for a separate blade. To facilitate this, the region of the seal through which the test strip will pass may be provided with a frangible line of weakness.

In a preferred embodiment, each test strip comprises a base member having a working area to which the fluid is to be applied, containing the reagent means, and a non-working area adjacent to the working area, wherein the total thickness of the test member in at least a portion of the non-working area is at least as great as the total thickness of the test member in the working area.

By making the non-working area at least as thick as the working area, scuffing or abrasion of the working area in a stack can be reduced. Moreover, if a compressive load is applied to a stack of the test members, this may be spread out over a greater area, thereby reducing the possibility of compressive damage to the working area.

In a preferred embodiment, at least a part of the non-working area is of greater total thickness than the thickness of the working area. This further reduces the likelihood of damage to the working area by scuffing or abrasion when in a stack. The difference in thickness is preferably from 1 to 20 µm, notably from 5 to 10 µm.

To build up the working area, a plurality of layers are sequentially applied to the base layer, for example by screen printing, typically with curing or drying steps between the application steps. The layers which are printed typically comprise electrode patterns, a reagent layer, and a mesh layer (for spreading out an applied fluid). As a result of the application of these layers, the working area of a conventional electrochemical test strip is typically about 100 µm thicker than the non-working area, which contains the electrode tracks and, typically, a dielectric layer. A stack of 100 test strips will therefore be about 10 mm thicker in the working area than in the non-working area. In a test strip in accordance with the present invention, at least a part of the non-working area may be made thicker by any suitable means. Suitable means include, for example: a printed relief ink; an applied pad or tape; embossing of the base layer or an intermediate layer; or an extension of the mesh layer from the working area.

Further objects and advantages of the invention will be apparent as the description proceeds.

BRIEF DESCRIPTION OF THE DRAWINGS

The invention will now be further described by way of example with reference to the following drawings, in which.

DETAILED DESCRIPTION

The test device shown in FIG. 1 comprises a housing 2 which houses a meter with a visible display 4, in this example, an LCD. A plunger 6 is released for use by the user pressing a release button which operates a catch. FIG. 1a shows the device after a user has depressed the release button with his right index finger. To take a reading of blood glucose concentration, the user partially depresses the plunger 6 to an intermediate position, causing a test strip to be presented for receiving a sample of blood (FIG. 1b). After the blood has been applied to the test strip, a reading is displayed on the display 4 (FIG. 1c). The user then fully depresses the plunger 6 so that it is again engaged by the catch, causing the test strip to be ejected. The device is then ready for another reading to be taken. FIG. 1d illustrates the device after the test strip has been ejected and after the user has again pressed the release button to free the plunger 6. The various mechanisms involved in this process will be described below.

Figure 1A:
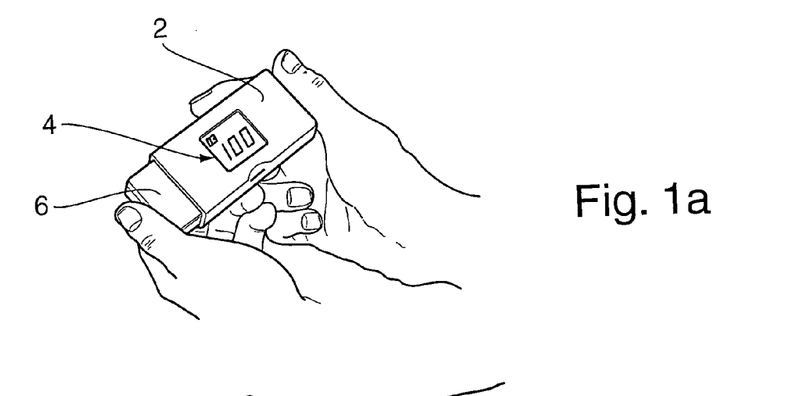
FIG. 1 illustrates user actions in operating a test device in accordance with the present invention.
Figure 1B:
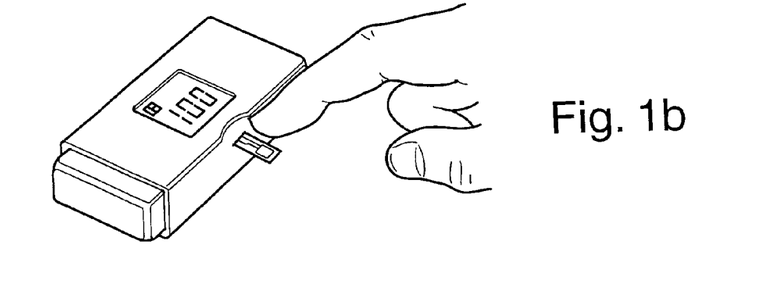
Figure 1C:
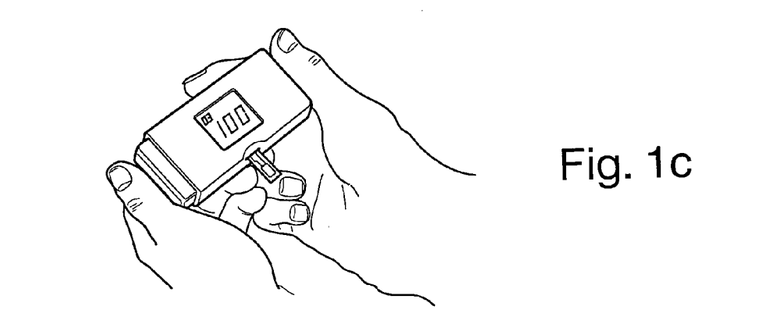
Figure 1D:
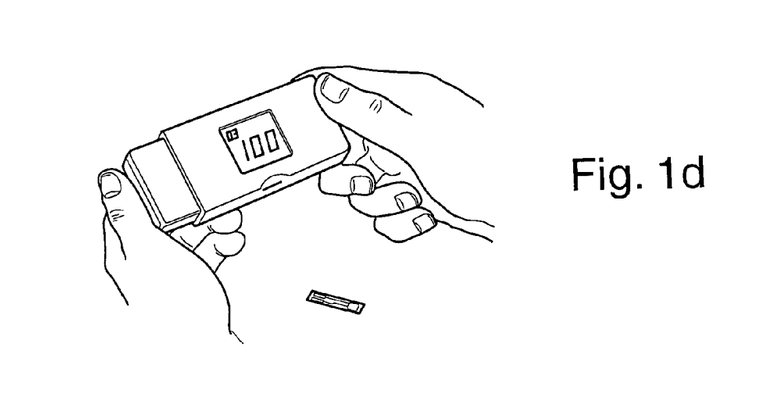
Figure 2:
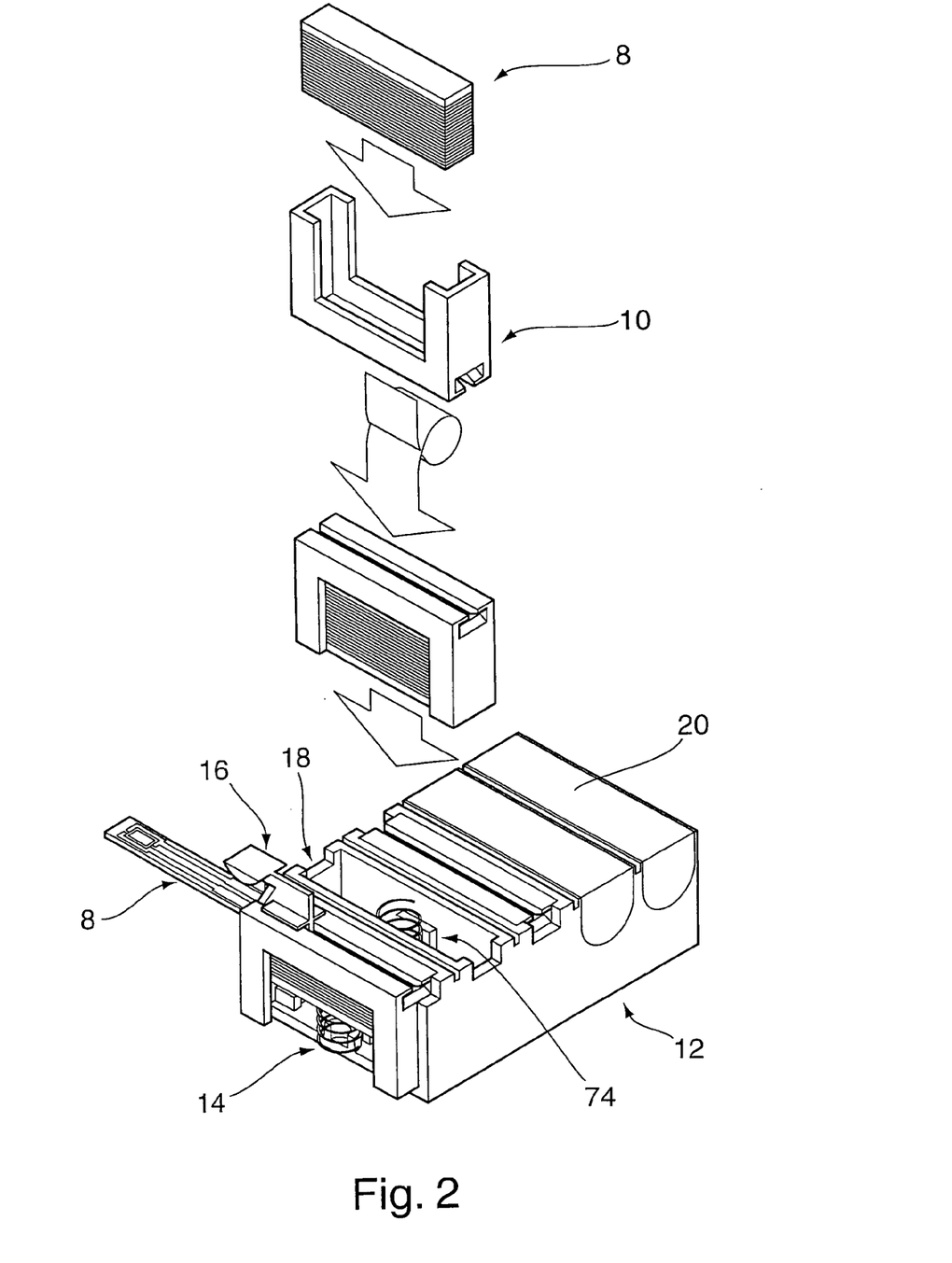
FIG. 2 shows the assembly of a cartridge for use in the device of FIG. 1.
Figure 3:
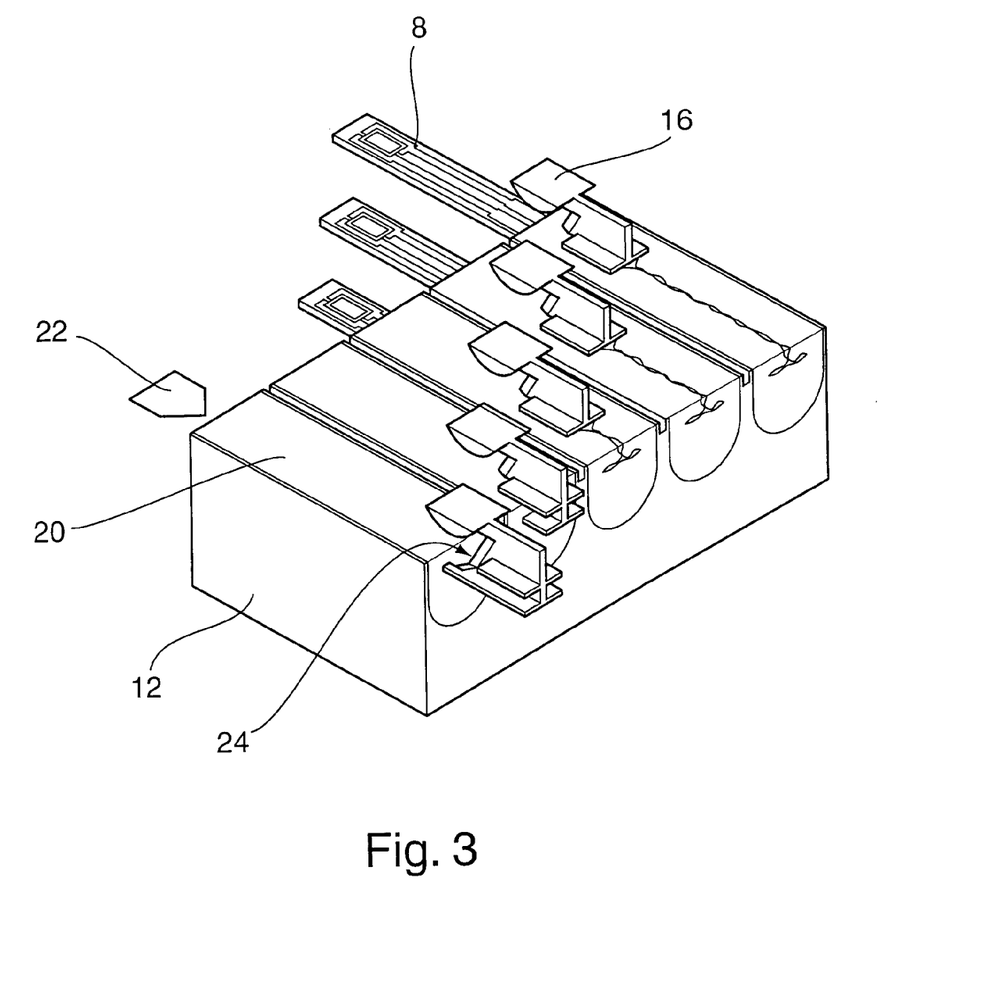
FIG. 3 illustrates the action of the pusher in opening the seal on a magazine.

As shown in FIG. 2, a stack of test strips 8 is loaded in a magazine 10, which is in turn located in cavity 74 in a cartridge 12. In this example there are five cavities 74, each of which houses spring means 14, in this example a helical spring. Each cavity has an opening 18 through which a test strip 8 will be pushed by a pusher 16. The spring urges the stack of test strips 8 upwards so that the top strip is engageable by the pusher 16. A foil seal 20 seals the cavities 74 containing the magazines 10. The slitting of the foil seal 20 will be described below, with reference to FIG. 3, which shows progressive movement of the pusher 16.

Advancement of the cartridge 12 moves it past a blade 22 which is mounted in the housing 2 of the test device. The blade 22 makes a slit in the foil seal 20 at one end, through which a test strip 8 is to be pushed. The pusher 16 is moved from one end of the cavity 74 to the other, as illustrated by positions (1) through (5) of FIG. 3. As the pusher 16 moves, cutting surfaces 24 on its leading edge cut the foil seal 20 and push the uppermost test strip 8 out through the opening 18 to the testing position (4) (corresponding to that shown in FIG. 1b), where a test reading can be taken. Fully depressing the plunger 6 moves the pusher 16 further towards the opening 18 and ejects the test strip 8. In subsequent drawings, the seal 20 is omitted for clarity.

Figure 4A:
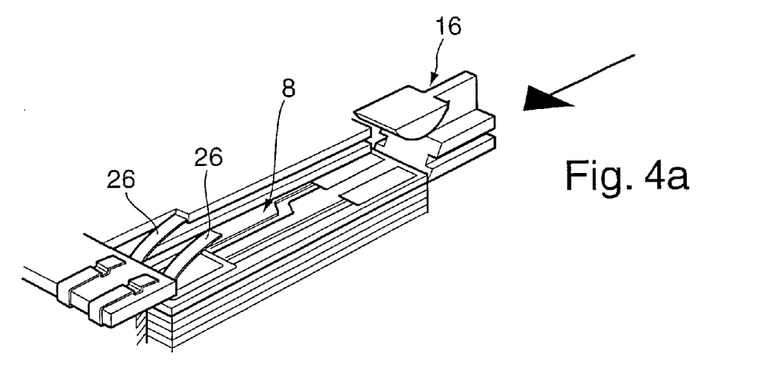
FIG. 4 illustrates the action of the pusher on a test strip.
Figure 4B:
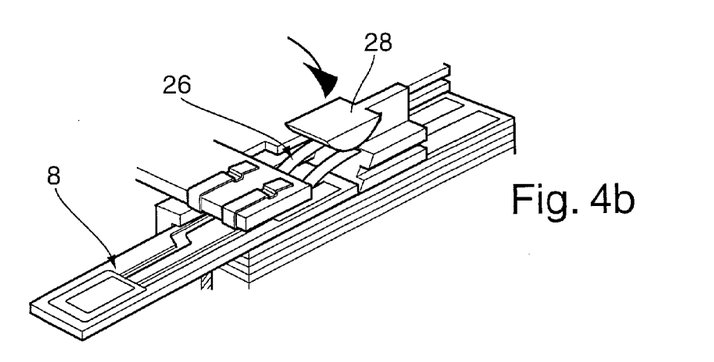
Figure 4C:
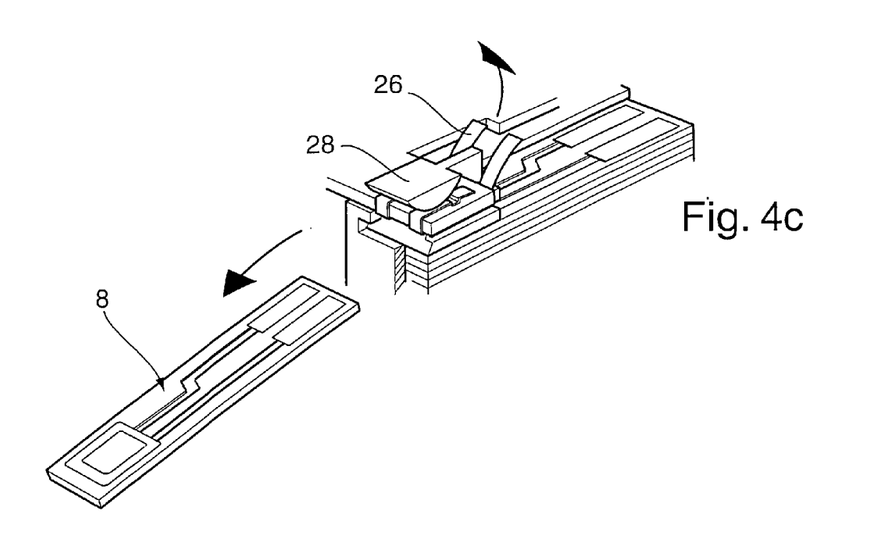
Figure 5A:
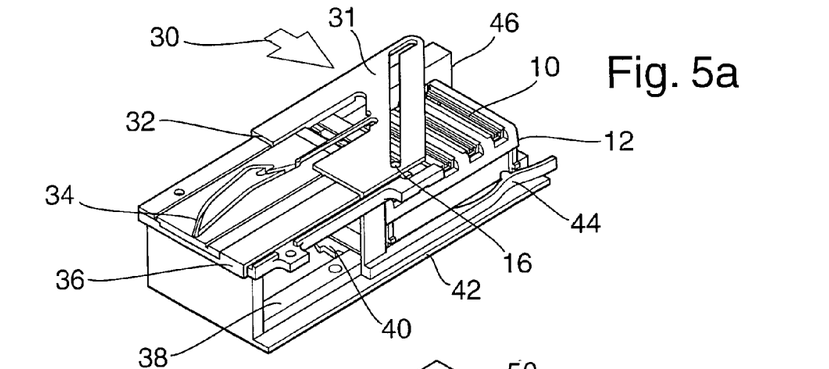
FIG. 5 shows a mechanism for operating the pusher.
Figure 5B:
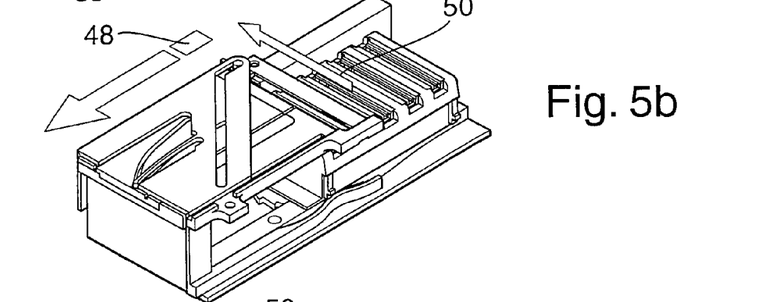
Figure 5C:
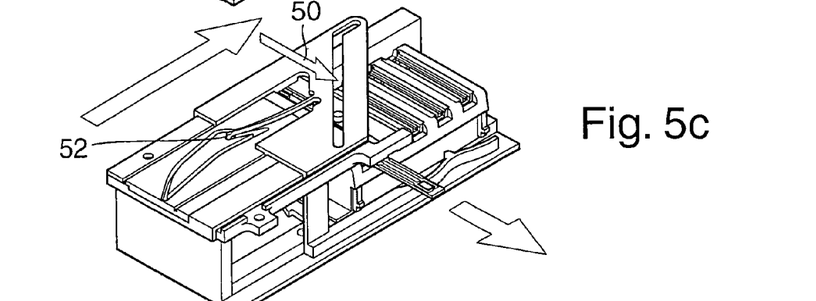
Figure 5D:
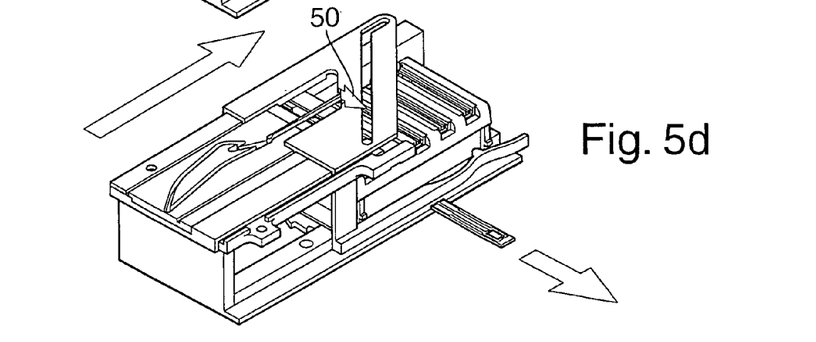

Referring now to FIG. 4, a mechanism is illustrated whereby movement of the pusher 16 from the position in FIG. 4a initially pushes the test strip 8 out of the housing and then the head 28 of the pusher 16 bears down on the electrodes 26 of the meter so as to bring them into engagement with electrode tracks on the test strip 8 (FIG. 4b). After a reading has been taken, further advance of the pusher 16 (FIG. 4c) takes the head 28 beyond the electrodes 26, which disengage from the test strip 8 and permit the pusher 16 to eject the test strip.

Figure 6:
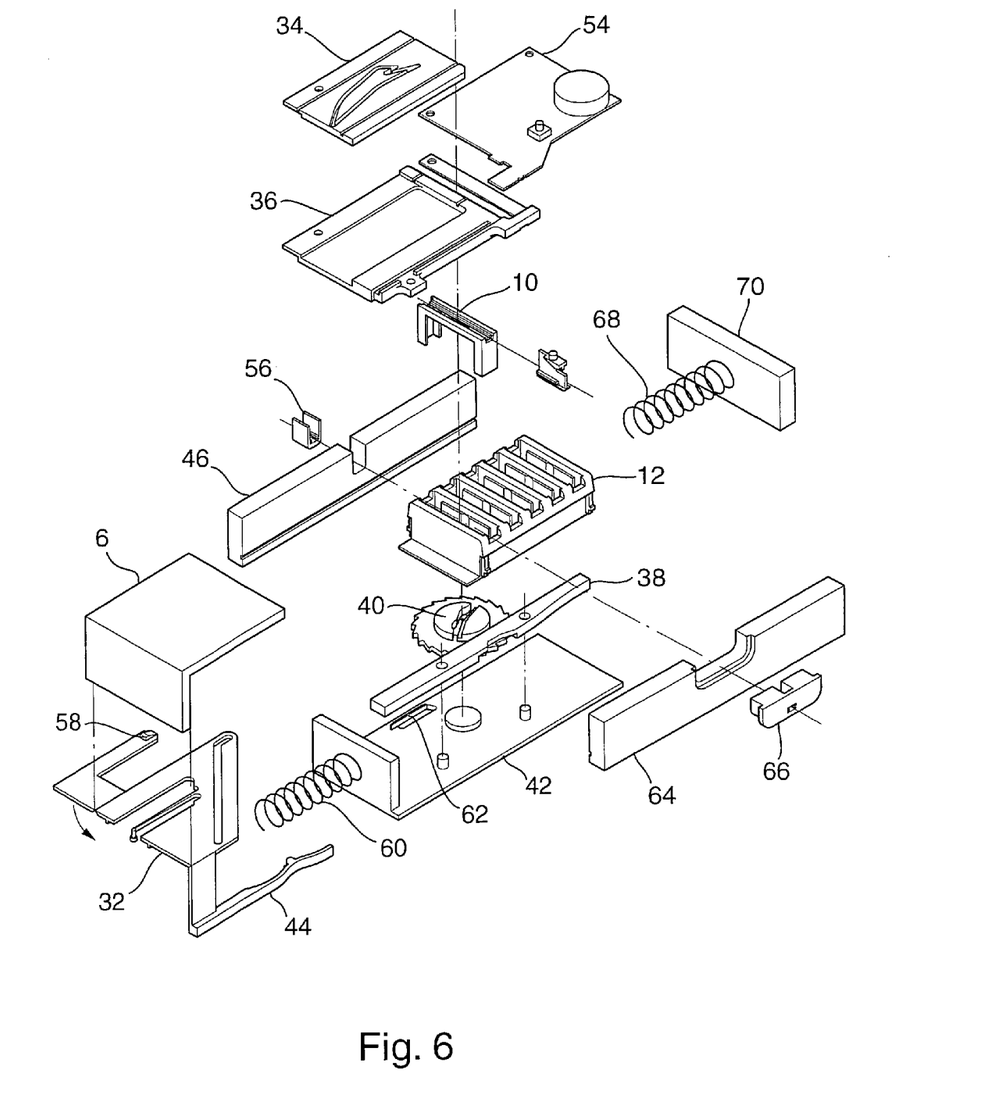
FIG. 6 is an exploded view of part of the device of FIG. 1.

The mechanism for advancing the pusher 16 is illustrated in FIG. 5. The assembly shown in FIG. 5 comprises a slider 32 which is operatively connected to the plunger 6. The slider 32 is slidably mounted on a chassis top 36 which receives a groove plate 34. The groove plate 34 has a groove therein which receives a sprung detent member 52 of the slider 32, the function of which will be described later. Also provided on the slider 32 is a ratchet driver 44 which engages with a ratchet wheel 40, the operation of which will be described later. A ratchet driver guide 38 is provided on the housing base 42. The back housing member 46 (and front housing member 64—FIG. 6) have cartridge tracks therein, along which the cartridge 12 can move. In the start position shown in FIG. 5*a*, the user presses the release button (not shown) where indicated by the arrow 30. This releases a catch 58 (FIG. 6) on the slider 32. A spring 60 (FIG. 6) pushes the plunger 6 and the slider 32 in the direction of the large arrow in FIG. 5*b*. The slider 32 has a hockey stick-shaped slot 31 in which is received the pusher 16. As the slider 32 travels, it moves the pusher 16 in the direction of the small arrow 50 shown in FIG. 5*b*. At 6 mm before the end of travel, the pusher 16 is removed from the cartridge 12. In the final 6 mm of travel the ratchet driver 44 indexes the ratchet wheel by one position, and advances the cartridge 12 so that the foil 20 on the first magazine 10 is slit at one end. The user then pushes the slider 32 to an intermediate position (FIG. 5*c*) and in so doing, causes the pusher 16 to move back, with its cutting surfaces cutting the foil as previously described, and pushing the uppermost test strip out of the housing 2. The slider 32 is held in the intermediate position by engagement of the sprung detent member 52 in the groove of the groove plate 34. The detent member 52 and groove plate 34 operate in the manner of a ballpoint pen advancing and retracting mechanism, with the detent member 52 cycling around the groove in the course of one test cycle. After a reading has been taken, the plunger 6 is then fully pushed in by the user (FIG. 5*d*), causing the slider to return to the position shown in FIG. 5*a* and causing the pusher to eject the used test strip 8. The slider 32 is now held in place until the next test reading is required. FIG. 6 shows some of the components more clearly, including the chassis cartridge end 70 which has a cartridge drive spring 68. A pusher "parking slot" plug 56 is mounted in the back housing member 46, where the pusher 16 is kept away from the cartridge 12 to permit movement of the cartridge. An optional sensor exit slot plug 66 is provided in the front housing member 64. A PCB 54 provides the meter electronics. When the test device is first used, and when a magazine is first opened up, a microprocessor on the PCB starts a timer counting down whereby the display 4 indicates when a particular magazine has exceeded its recommended life, or in the event that all magazines have exceeded their shelf life.

Figure 7:
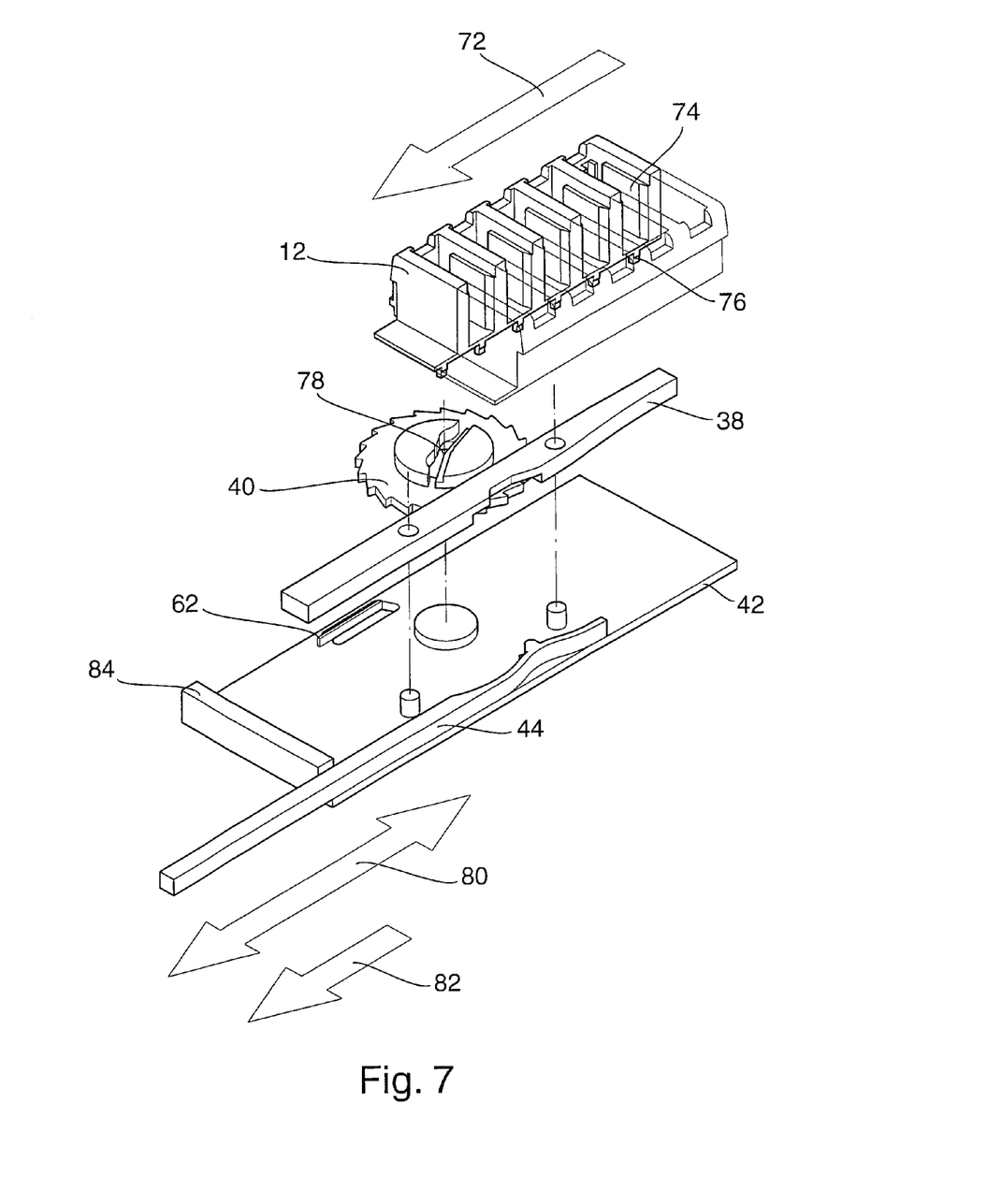
FIG. 7 is an exploded schematic view illustrating the cartridge advance mechanism.

FIG. 7 shows the cartridge advance mechanism as an exploded schematic, with the cartridge in half-section. The cartridge 12 is urged by the spring 68 in the direction of the arrow 72. Underneath the cartridge 12 there is provided a plurality of cartridge location pegs 76, which are spaced apart by the width of the magazines, ie the distance between the centre lines of the magazines 10. There is a peg 76 for each cavity 74, and an additional leading peg on a front lip of the cartridge 12. The ratchet wheel 40 has a keyway 78 thereon for the cartridge location pegs 76 to pass through as the cartridge 12 advances. The ratchet wheel is driven by the ratchet driver 44 which, cooperating with a pawl 62, drives the ratchet wheel 40 in a clockwise direction as viewed in FIG. 7. The ratchet driver 44 reciprocates in both directions (80), but is sprung only in the direction indicated by the arrow 82. A cartridge final stop member 84 is provided at the proximal end of the housing base 42.

Figure 8A:
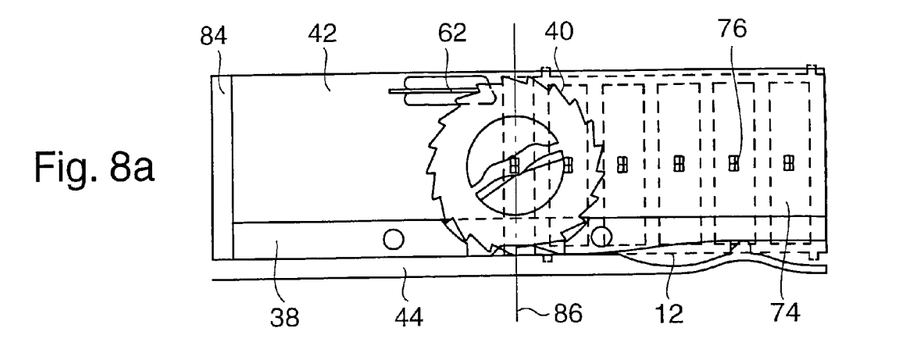
FIG. 8 shows steps in the advance of a cartridge.
Figure 8B:
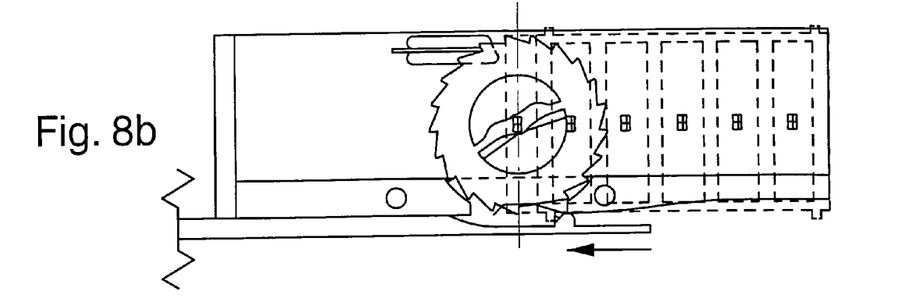
Figure 8C:
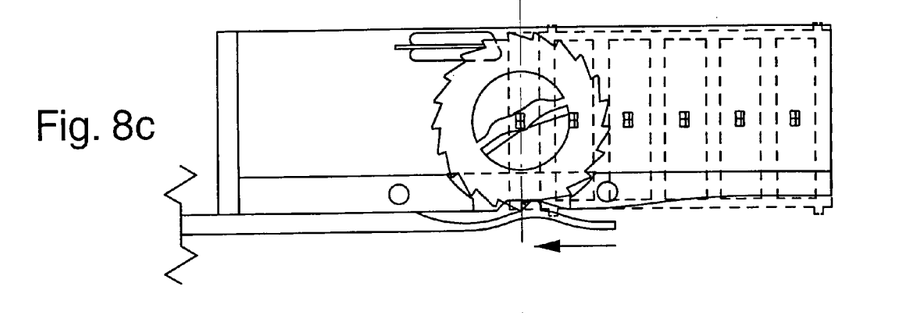
Figure 8D:
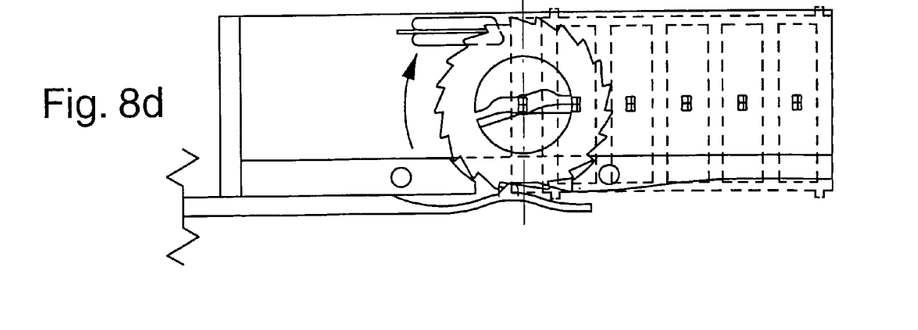
Figure 8E:
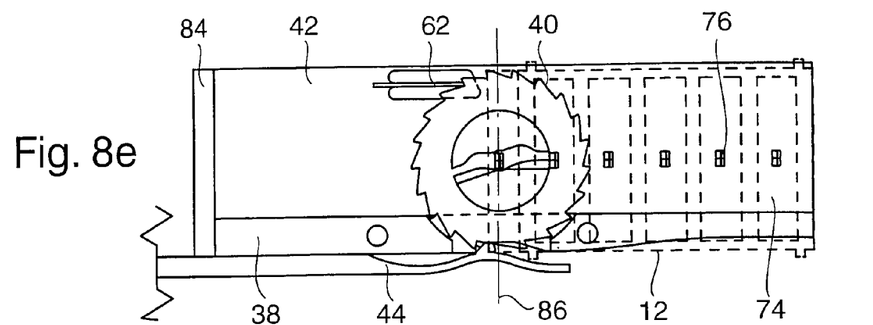
Figure 8F:
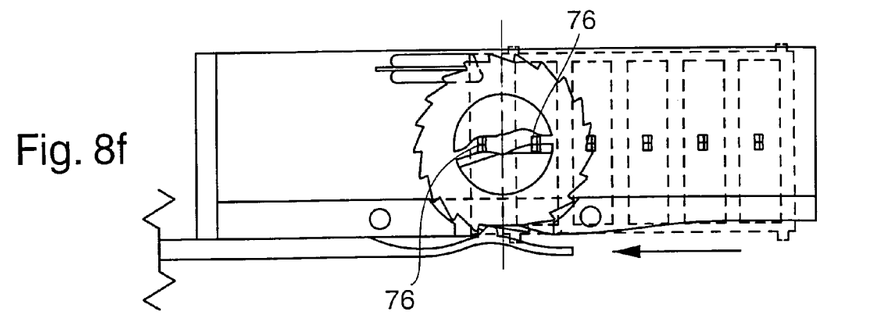
Figure 8G:
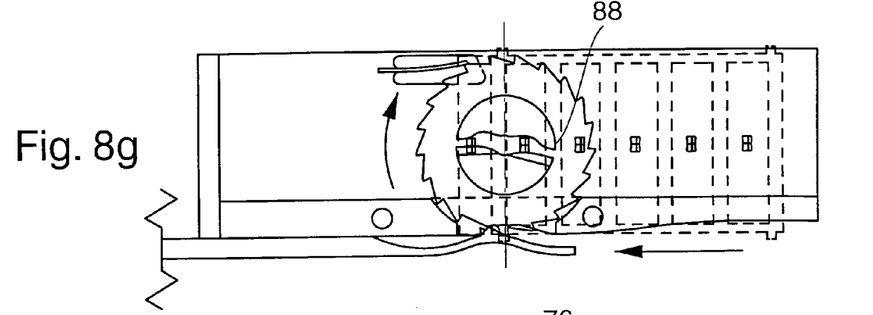
Figure 8H:
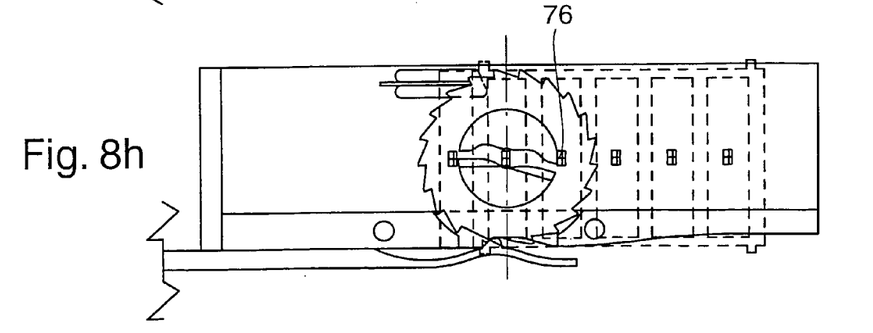

After each advance of the cartridge 12, it remains stationary until the test strips in a magazine have been used up. At this point the cartridge 12 advances by the width of a magazine. The mechanism for controlling advance of the cartridge 12 is described with reference to FIGS. 8 and 9. Starting from the position shown in FIG. 8*a*, the ratchet mechanism is in a rest position ready for use. The centre line 86 of the active magazine 12 is in the keyway of the ratchet wheel 40. The user presses the release button and the ratchet driver 44 travels in the sprung direction (arrowed—FIG. 8*b*). The ratchet driver 44 engages the ratchet wheel (FIG. 8*c*) and rotates or indexes the ratchet wheel by one place (arrowed—FIG. 8*d*). FIGS. 8*d* through 8*h* shows the cartridge advancement sequence. As the ratchet wheel 40 advances from the position shown in FIG. 8*e* to that of FIG. 8*f*, the two foremost location pegs 76 of cartridge 12 are freed to advance through the keyway 78. The location peg 76 furthest to the left in FIG. 8*f* acts against the inclined surface of the keyway 78 while exiting the keyway. This forces the ratchet wheel 40 to rotate one place (FIG. 8*g*) while the second location peg 76 is moved to the centre of the ratchet wheel. The rotation of the ratchet wheel 40 presents a solid stop wall at the point 88 to the oncoming location peg. At the position shown in FIG. 8*h*, the cartridge has advanced by one magazine width, and the location peg 76 of the magazine behind the new active magazine comes to rest against the ratchet wheel stop wall, aligning the next magazine ready for use.

When the cartridge 12 is loaded in the housing during manufacture, the front location peg 76 is located in the keyway 78 and the ratchet wheel 40 is located so that the first time the ratchet wheel is indexed, the foremost magazine 10 is advanced as describe above, and the seal is cut by the blade 22.

Figures 8I, 9A:
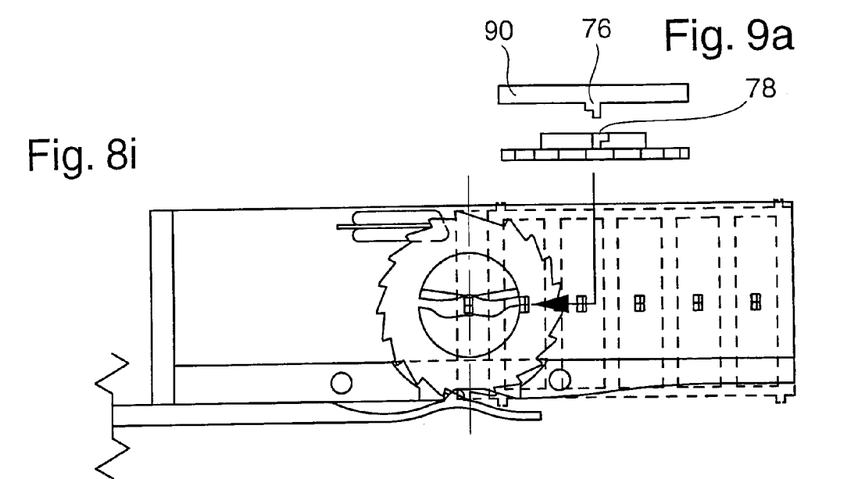
FIG. 9 shows sectional views through part of the cartridge advance mechanism at different stages.
Figures 8J, 9B:
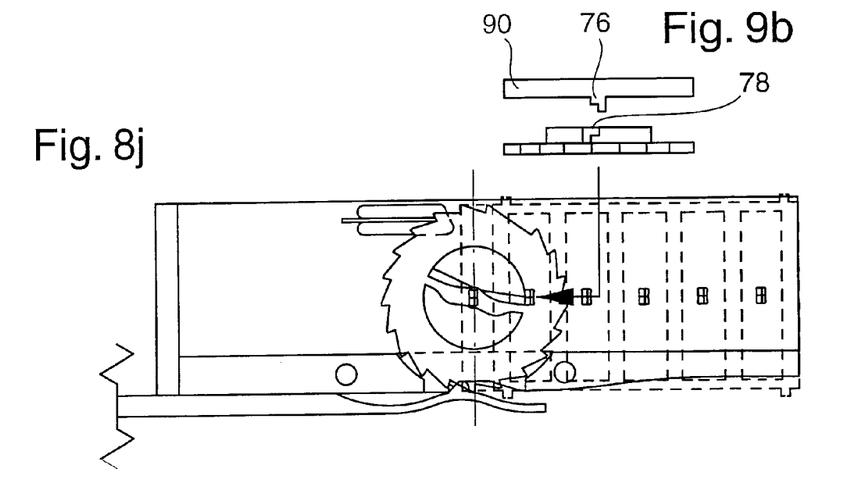

Because there are 20 test strips per magazine, and 20teeth on the ratchet wheel, the ratchet wheel is constructed to permit cartridge advance only once during a complete (360°) rotation. FIGS. 8*i* and 9*a* show how, with the ratchet wheel at position 10 (180° rotation), the cartridge 12 is prevented from premature advancement. The cartridge location peg 76 is prevented from entering the ratchet wheel keyway 78 through incorrect orientation and misalignment. The cartridge base 90 and location peg 76 are shown separated from the ratchet wheel in FIGS. 9*a* and 9*b* for clarity. With the ratchet wheel at position 11 (FIGS. 8*j* and 9*b*) the location peg 76 is also misaligned with the ratchet keyway 78 and the cartridge does not advance.

Figure 10A:
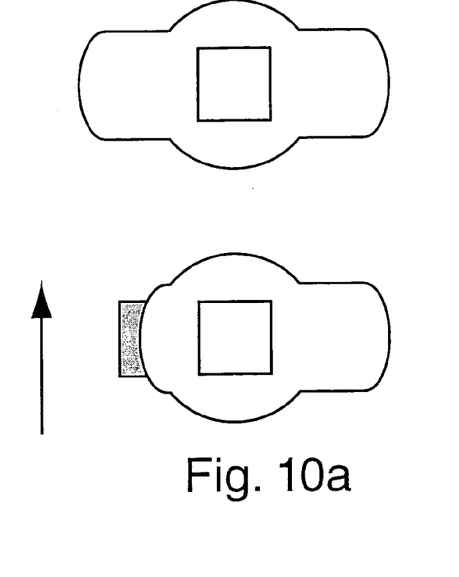
FIG. 10 illustrates an alternative embodiment in which magazines are releasably connected together.
Figure 10B:
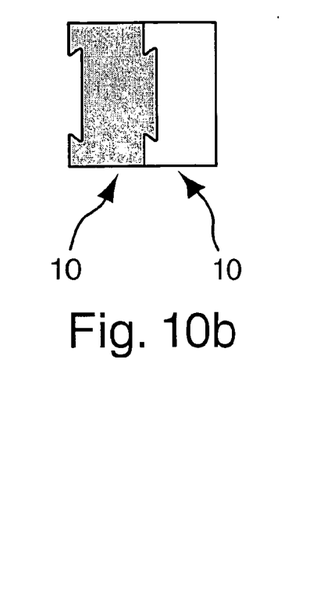

An alternative embodiment is illustrated with respect to FIG. 10. Here, the magazines are releasably connected together, in this example by a dovetail joint (FIG. 10*b*). Used magazines 10 project through an opening in the housing and can be removed by the user. FIG. 10*a* shows plan views before (top) and after (bottom) a used magazine has been slid off from its neighbour. In this embodiment the housing can be made smaller because it need not accommodate used magazines.

Figure 11:
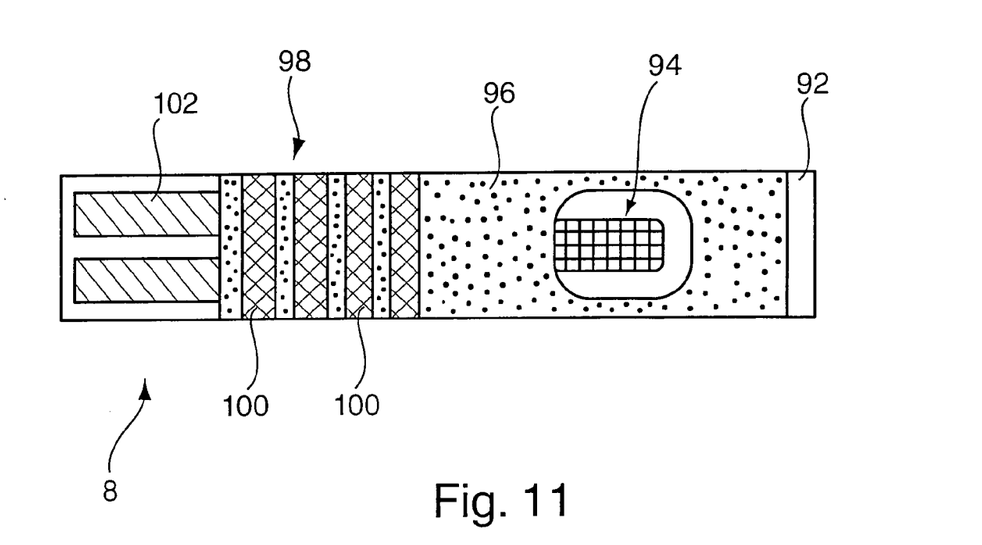
FIG. 11 is a top plan view of a test strip in a preferred embodiment of the invention.

The test strip 8 shown in FIG. 11 comprises a planar base member 92, in this example of poly(butylene terephthalate) (PBT) (Valox® FR-1 from GE Plastics). The strip is 30 mm×5.5 mm, and 0.5 mm thick. A working area 94 is of conventional construction, comprising a plurality of electrodes, a reagent layer in intimate contact with the electrodes, and a mesh layer for spreading out a drop of fluid to be received on the working area. Electrode tracks 102, for example of carbon, in the non-working area 98 of the test strip are connected to the electrodes in the working area 94 in known manner. Also in known manner, a dielectric layer 96 is printed around the working area 94 so as to overlie a portion of the electrode tracks 102, leaving just the ends of the tracks exposed for connection to corresponding 26 electrodes on the meter. The layers are applied to the base member as inks, by screen printing. Each ink layer is about 10 to 20 µm thick, and the mesh is about 59 to 67 µm thick. The working area 94 has a total thickness which is about 100 µm thicker than the non-working area 98 up to the dielectric layer 96.

To increase the thickness of parts of the non-working area, a high relief ink 100 has been printed in four strips. The high relief ink has a dried thickness such that the total thickness of the non-working area to which the high relief ink 100 has been applied is slightly greater than the total thickness of the test strip in the working area 94. Thus, when a stack of such test strips 8 is formed, and a compressive load is applied to the stack by the spring 14, the working area 94 will not bear all the compressive load. Scuffing of the test area will be reduced compared to a conventional test strip in which the working area stands proud of the non-working area.

Although this embodiment has been illustrated with reference to the use of a high relief ink printed in strips, it will be understood that it is not limited to this embodiment. The ink could be printed as a continuous block, and it could entirely surround the working area if desired. Instead of, or in addition to, the high relief ink, other means could also be provided to increase the thickness of the non-working area, for example: an applied pad or tape; embossing of the base layer or an intermediate layer; or an extension of the mesh layer from the working area into the non-working area.

Although the invention has been described with reference to a test device for measuring blood glucose concentration, it is to be understood that the invention is not limited to this application. The invention may be used in the determination of any analyte in a fluid by the use of suitable reagents in the test strip. Such reagents are well known to those skilled in the art.

The invention claimed is:

1. A test device for testing of analyte concentration in a fluid to be applied thereto, the device comprising:
   a) a plurality of test members arranged in at least a first stack, each of said test members carrying reagent, each of said test members having a plurality of electrode tracks that are adapted and configured to conduct an electrical signal;
   b) a housing having electrodes disposed therein that are adapted and configured to engage the electrode tracks of each of the test members of the first stack when such test member is positioned at an engagement location;
   c) a meter operatively connected to the electrodes of the housing and disposed at least partly in the housing;
   d) a pusher which is adapted to pushably move each of the test members in turn at least partially from the first stack and into the engagement location where such test member will engage with the electrodes of the housing and where such test member can be accessed to apply a fluid to the reagent of such test member;
   e) an actuation member operably connected to the pusher, the actuation member being operable by a user to move the pusher relative to the housing;
   f) the first stack being contained in a magazine which is initially sealed by a moisture impermeable seal; and
   g) a blade, the magazine being movable relative to the housing from an initial position where the seal is intact to a position where the pusher can push a first one of the test members from the first stack, the movement causing the blade to cut the seal in a manner forming a slit through which the first test member is able to pass through as first test member is pushed by the pusher toward the engagement location.

2. A device as claimed in claim 1, further comprising second and third stacks, each of the second and third stacks comprising a plurality of test members, each of said test members carrying reagent and having a plurality of electrode tracks that are adapted and configured to transmit an electrical signal, each of the second and third stacks being contained in a magazine which is initially sealed by a moisture impermeable seal, each of the magazines being movable relative to the housing in a manner such that movement of said magazine causes the blade to slit the seal of said magazine as said magazine is moved to a position where the pusher can push one of the test members of said magazine toward the engagement position.

3. A device as claimed in claim 1, wherein the actuation member is configured and adapted in a manner such that operation of the actuation member causes the pusher to engage with the electrodes of the housing and bring the electrodes of the housing into contact with the electrode tracks on each of the test members when such test member is in the engagement location.

4. A device as claimed in claim 3, wherein the actuation member is configured and adapted in a manner such that further operation of the actuation member causes the pusher to push such test member from the engagement location and eject such test member from the housing.

5. A device as claimed in claim 1, wherein the pusher comprises at least one cutting surface that is adapted and configured to cut the seal.

6. A device as claimed in claim 2, further comprising a cartridge that houses each of the magazines and that is moveable relative to the housing.

7. A device as claimed in claim 6, wherein the device further comprises a ratchet wheel having a keyway, and wherein the cartridge is biased against the ratchet wheel and comprises a plurality of spaced apart location pegs configured and adapted to locate in the keyway, and the ratchet wheel is configured and adapted to permit any one of the location pegs to locate in the keyway only when the ratchet wheel is in a orientation relative to the cartridge.

8. A device as claimed in claim 7, wherein the actuating member is configured and adapted to cause the ratchet wheel to rotate in a manner indexing the keyway of the ratchet wheel with one of the location pegs of the cartridge.

9. A device as claimed in claim 1, further comprising a sliding member having an angled slot therein, the angled slot having a cam surface that bears against the pusher, the sliding member being configured and adapted in a manner such that movement of the sliding member in a first direction causes movement of the pusher in a second direction.

10. A device as claimed in claim 1, further comprising a biasing member that biases the stack of test members towards the seal.

11. A device as claimed in claim 1, wherein the pusher is adapted and configured to be releasable detained in position relative to the housing one of the test members is in the engagement location.

12. A device as claimed in claim 1, further comprising a timer and a display, the timer being configured and adapted to track the duration of time that passes from the breaking of the seal of the magazine by the blade, the display being operatively connected to the timer and being configured and adapted to visibly display indicia indicative of expiration of the useful life of the test members as a result of time that passes from the breaking of the seal of the magazine by the blade.

13. A device as claimed in claim 1, wherein the reagent is adapted and configured to react with blood glucose.

14. A device as claimed in claim 2, wherein the magazines are releasably connected together and wherein the housing has an opening through which each of the magazines can pass through after being separated from the other of the magazines.

15. A device as claimed in claim 1, wherein each test member in the first stack consists of a working portion that is defined by the reagent and a non-working portion, the working portion has a maximum thickness, and the non-working portion has a maximum thickness that is at least as great as the maximum thickness of the working portion.

16. A device as claimed in claim 15, wherein the maximum thickness of the non-working portion is greater than the maximum thickness of the working portion.

* * * * *